United States Patent
Lu et al.

(10) Patent No.: US 6,683,305 B1
(45) Date of Patent: Jan. 27, 2004

(54) METHOD TO OBTAIN TRANSPARENT IMAGE OF RESIST CONTACT HOLE OR FEATURE BY SEM WITHOUT DEFORMING THE FEATURE BY ION BEAM

(75) Inventors: Wei Lu, Poughkeepsie, NY (US); Charles N. Archie, Granite Springs, NY (US); Chester Wasik, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 10/274,599

(22) Filed: Oct. 18, 2002

(51) Int. Cl.7 ............................................. G01N 23/04
(52) U.S. Cl. .................. 250/307; 250/309; 250/492.1; 250/492.2
(58) Field of Search .................. 250/307, 309, 250/311, 492.21, 492.2, 492.1

(56) References Cited

U.S. PATENT DOCUMENTS

| 4,939,364 A | 7/1990 | Ishitani et al. |
| 5,028,780 A | 7/1991 | Kaito et al. |
| 5,093,572 A * | 3/1992 | Hosono ........................ 250/307 |
| 5,656,811 A * | 8/1997 | Itoh et al. ..................... 250/309 |
| 5,780,852 A | 7/1998 | Shu |
| 5,986,264 A * | 11/1999 | Grunewald .................. 250/310 |
| 6,140,603 A | 10/2000 | Hwang et al. |

FOREIGN PATENT DOCUMENTS

JP          5-347344          12/1993

* cited by examiner

Primary Examiner—John R. Lee
Assistant Examiner—James P. Hughes
(74) Attorney, Agent, or Firm—Scully, Scott, Murphy & Presser; Todd M. C. Li

(57) ABSTRACT

A method and arrangement of obtaining a transparent image of a resist contact hole or feature provided on a silicon wafer through a scanning electron microscope (SEM), with an absence of deforming the feature, such as the contact hole. In particular, the method is directed to the obtaining of a transparent image of a resist contact hole or feature by SEM without damaging the silicon wafer.

14 Claims, 5 Drawing Sheets

METHOD TO OBTAIN TRANSPARENT IMAGE OF RESIST CONTACT HOLE OR FEATURE BY SEM WITHOUT DEFORMING THE FEATURE BY ION BEAM

BACKGROUND OF THE INVENTION

1. Field of the Invention

The present invention relates to a method of obtaining a transparent image of a resist contact hole or a feature in a resist provided on a silicon wafer through a scanning electron microscope (SEM), with an absence of deforming the feature, such as the contact hole, by a focused ion beam (FIB). In particular, the method is directed to the obtaining of a transparent image of a resist feature, such as a contact hole, by SEM without damaging the silicon wafer, and to obtain an accurate characterization of measurements of hidden features in the resist.

In the current technology which is utilized in process development and failure analysis during semiconductor manufacturing, it is of importance to be able to obtain cross-sections of critical structures which are located on a silicon wafer. Thus, the cross-section of holes or other two-dimensionally restricted features are particularly subject to problems, inasmuch as it is difficult to dice or cleave the silicon wafer precisely though the center of a given contact or feature Moreover, the loss of time involved with off-line cross sectioning of the silicon wafer, attendant by the loss of the entire wafer and the effecting of only a limited number of samplings on a given silicon wafer are all negative aspects which adversely affect the economics of such sampling or testing methods, the latter of which are essentially of a destructive nature.

In addition to conventional cross sectioning and subsequent scanning electron microscope (SEM) viewing of a feature or sample on a silicon wafer at essentially right angles thereto, the focused ion beam (FIB) system has been developed to essentially produce local milling operations which enable a considerable amount of the critical information to be gathered for various diverse situations. At this time, FIB techniques for the local milling of holes; for example such as selective carbon mill (SCM) necessitate the milling away of up to half of the hole. This is subject to considerable inaccuracies in determining the true diameter of the hole of the silicon wafer, and even more importantly, may result in the deformation of the structure by the milling process due to the direct contact of the focused ion beam with the structure of interest or feature in the silicon wafer.

2. Discussion of the Prior Art

In essence, the current technology employs the following processes:

a) Mechanical cleavage of the wafer, which consists of physically braking the wafer, and then obtaining an SEM image of the broken cross-section. This generates two problems in that, firstly, the wafer is destroyed, and secondly, the features can be deformed during cleavage. This deformation is partially addressed by depositing a metal layer (such as gold) over the surface, which adds to the cost and adversely affects the economics of the process.

b) FIB with gas assisted etching (GAE) is used to perform the milling; wherein GAE is a standard technique that includes the use of a gas, such as H2O vapor, during the milling to carry away carbon or other components to prevent re-deposition on the cross-section. This procedure is less destructive than mechanical cleavage. This technique mills away a selected portion of the resist, preferably through the center of the features (such as contact holes), leaving a cross-section which is imaged by SEM, and does not destroy the wafer substrate, so that at minimum, other portions of the wafer may be used. However, there may be encountered deformation of the features during milling of the resist. In addition, accurately locating the position of the region to be milled typically a rectangular cutout shape, where on edge of the rectangle is targeted to cut through the center of the features such as contact holes is difficult to obtain because charge accumulation tends to cause deflection of the ion beam. This milling selection process typically involves a rapid FIB scan at low beam energy to obtain an image, and then selection of a milling region (e.g. a rectangular region having an edge overlaying a line of contact holes). Because of deflection, also referred to as drift, due to charge accumulation, which can occur both during FIB imaging as well as during FIB milling the edge of the milling region is frequently selected to cross the line of contact holes at an angle, such as 3 degrees, in order to ensure that at least some of the holes are cross-sectioned across the center of the hole.

In contrast with the state-of-technology, the present invention allows the imaging of hidden features in resist without distortion of the features, avoids the problem of inaccurate milling due to charge effects (i.e., deflection or drifting of the ion beam), and does not require any mechanical cleavage of the wafer.

SUMMARY OF THE INVENTION

Accordingly, in order to clearly and unambiguously distinguish over the state-of-the art, pursuant to the present invention there is utilized a method of non-destructive testing; wherein there is obtained an accurate measurement of hidden features in resist, such as contact holes, by means of the obtaining of a transparent SEM image.

Essentially, the inventive method comprises the steps of:

Milling a section of resist, in which the edge of the milled region is offset from the features of interest by about 300 nm or less (in effect, creating a cross-section resist where there is about 300 nm of resist between the exposed cross-section plane and the edge of the feature). The offset is preferably within the range of about 100–200 nm.

Image the cross-section using an SEM between about 3–20 kev, preferably 5 kev to 17 kev.

It is the high energy SEM which provides the transparency of the image to enable a view of the hidden feature profile. The offset cross-section means that the features will be subject to little or no distortion. It is also easier to accurately target an offset milling region because the accuracy of the milling location will be less affected by drift or deflection caused by charge accumulation.

The advantages which are derived by the inventive method:

a) Saving the wafer for further production or further analysis because no mechanical cleavage of the resist wafer is necessary.

b) Using the transparency of the resist to obtain the SEM image of contact profile can eliminate the ion beam damage sustained at the edges of contact hole or resist features during regular cross-section cutting, and increases the SEM image fidelity while preserving the true profile.

c) This method has short cycle time compared with a mechanical cleaving process, and provides precise controlling over the cross-section location.

In particular, the tooling employed through the metrology of the resist provides the advantages over regular mechanical cleaving processes through the saving of the silicon wafer, reduction in cycle time and enhanced control over the positioning wherein any ion-caused damaged (due to FIB) during cutting is a concern which is solved by the present invention. In effect, the present invention uses advantages, which clearly improves over the prior art as employed in the current state of the technology.

FIB milling is used to provide side view access near the hole in the silicon wafer but not to touch the hole, thereby avoiding the issue of deforming the structure. The remaining material is less than 0.25 um, whereby thinner is better.

Electron beam is sufficiently energetic to pass through the remaining material to the actual hole, where secondary electrons are generated that can escape from the hole and be detected.

Because of the thinness of the remaining material, the primary beam is subject to only very little deflection, thereby accurately identifying the edges of the hole.

The extremes of the hole extension (diameter) are particularly well defined because these surfaces are naturally parallel to the beam and provide a maximum surface for the prime penetrating electron beam which, in turn, provides maximum production of secondary electrons.

For resist materials, SEM image starts to show transparency properties when the beam energy is higher than 3 kev. Relatively higher electron beam energy can be used to obtain smaller beam spot size, more signal, high resolution image, and deeper transparency of the features because of the above charge elimination techniques.

Because of this protective cross-sectioning technique, it can be used for contact hole or hidden feature of the most diverse sizes, for example, such as approaching 100 nm or even smaller, although not limited thereto.

Accordingly, it is an object of the present invention to provide a novel method which will obtain the image of resist contact holes or resist features on a silicon wafer by scanning electron microscope (SEM) without the deformation of the feature or features by a focused ion beam (FIB).

A more particular object of the present invention resides in the provisions of the method as described herein wherein there is employed an SEM operating at a specified beam energy, and which enables the SEM image to display transparency properties.

BRIEF DESCRIPTION OF THE ACCOMPANYING DRAWINGS

Reference may now be made to the following detailed description of preferred embodiments of the invention, taken in conjunction with the accompanying drawings; in which.

DETAILED DESCRIPTION OF PREFERRED EMBODIMENTS

Figure 2:
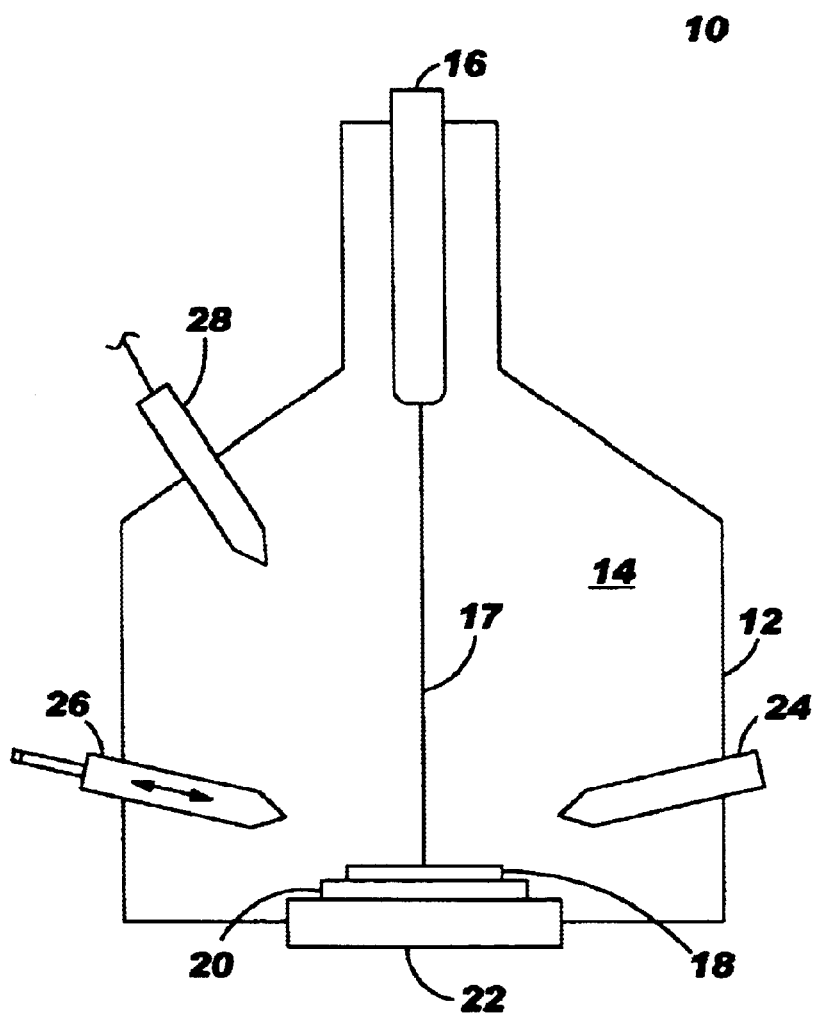
FIG. 2 illustrates, generally diagrammatically, a typical dual-beam milling tool including a focused ion beam (FIB) system and scanning electron microscope (SEM) metrology.

As illustrated in FIG. 2, a scanning electron microscope (SEM) 16 extends into the chamber 14 through the wall of housing 12 at an angle of tilt relative to a focused ion beam FIB tube 28 and a horizontal surface of a test specimen tube 18. Also extending into the chamber 14 so as to face towards the sample or test specimen 18 is a movable nozzle 26 for the optional introduction of $H_2O$ in a preferably vaporous condition. A further nozzle 24 also extends into the vacuum chamber 14 through the wall of housing 12, and is adapted to optionally introduce a gas, such as gaseous $XeF_2$ into contact with or proximity to the sample or test specimen 18.

Figure 1:
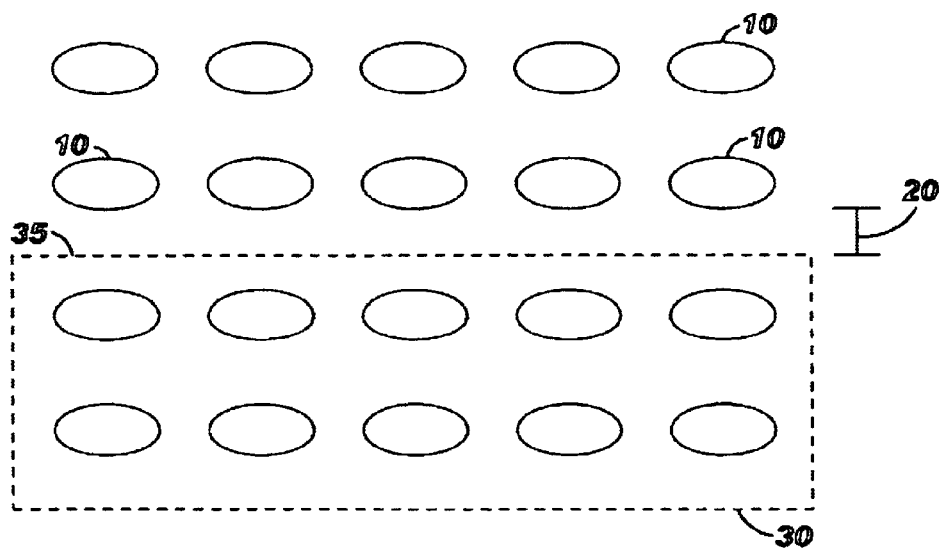
FIG. 1 illustrates, diagrammatically, a plane view of contact holes formed in a resist layer.

The foregoing is illustrated by a sketch such as represented in FIG. 1. FIG. 1 is a plane view of contact holes 10 in a resist layer. A region 30 is selected for milling, where the edge 35 of the target milling region is offset from the edge of the target features, which are a line of contact holes in this example, by a distance 20 that is less than about 300 nm, preferably 100–200 nm. Generally, thinner is better for transparency, but the thinness of the wall will be limited, for example, by its mechanical strength. Optionally, this technique may be used to image a target that may be an interior portion of the contact holes, so that the target milling region may cut into the feature, i.e. the contact hole, but offset from the target region of the portion of the feature to be imaged.

Figure 3B:
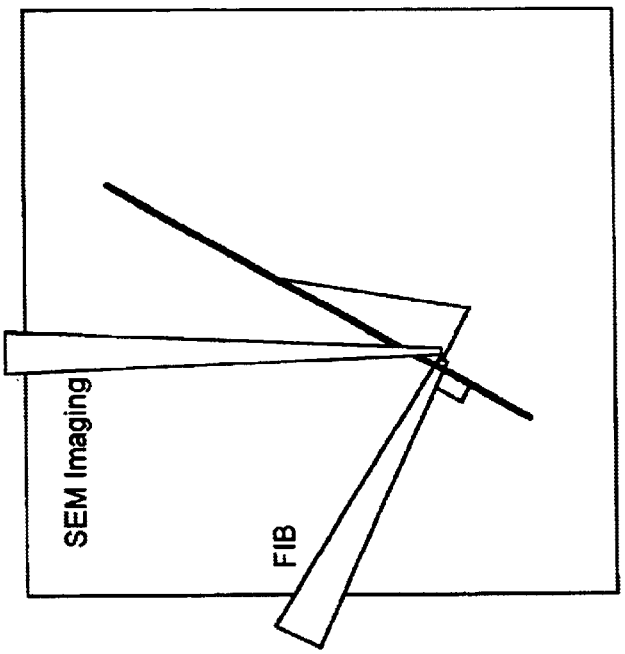
FIGS. 3A and 3B illustrate a schematic representation as to the configuration of the SEM tube limiting the tilting angle of the wafer.
Figure 3A:
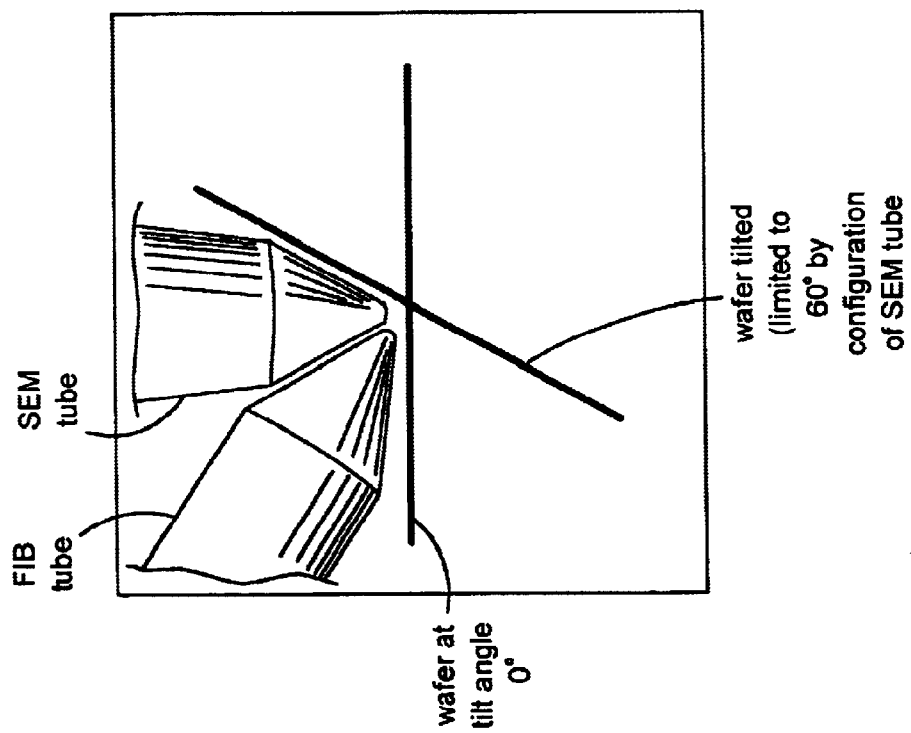

It is noted that the 52 degree tilt mentioned in the above-referenced discussion is really a function of the standard configuration of dual beam tools (refer to FIGS. 3A and 3B). Typically, the wafer is milled by the FIB beam with the wafer tilted at an angle which is limited by the configuration of the tool, and then rotated to be imaged by the SEM beam. The tool configuration limits the maximum tilt angle to about 60 degrees. Preferably, the SEM beam should be aimed at the highest angle possible to obtain the best image, relative to the cross-sectioned face. SEM magnification of 200,000 is just a standard magnification.

Figure 4:
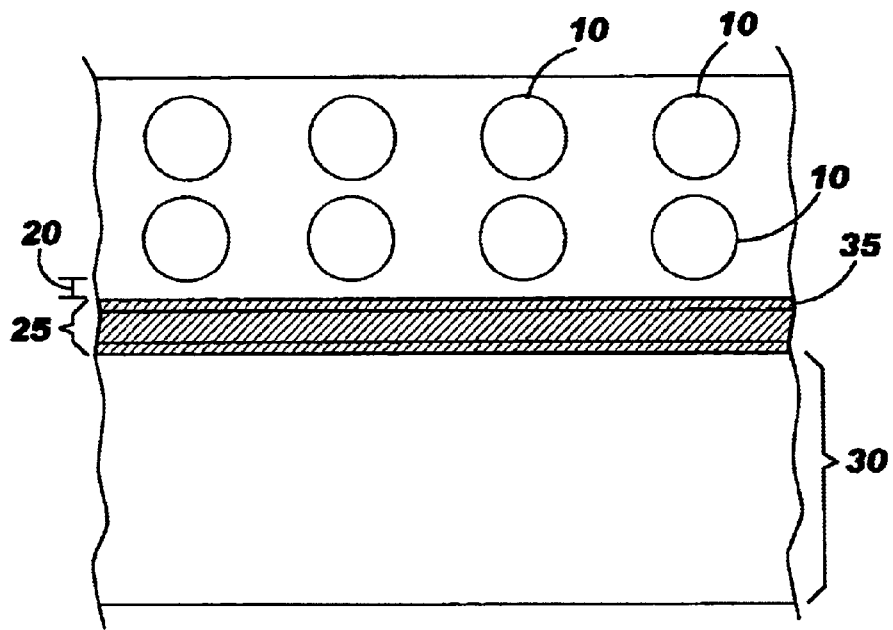
FIG. 4 illustrates a top view of an SEM image of a resist layer.

FIG. 4 is an SEM image showing a top down view (0 deg tilt) of a resist layer having contact holes 10, a milled region 30 having an edge 35 offset by distance 20 from the edge of a line of contact holes. The milled region 30 has had the resist removed, and a cross-section area 25 is exposed.

Figure 5:
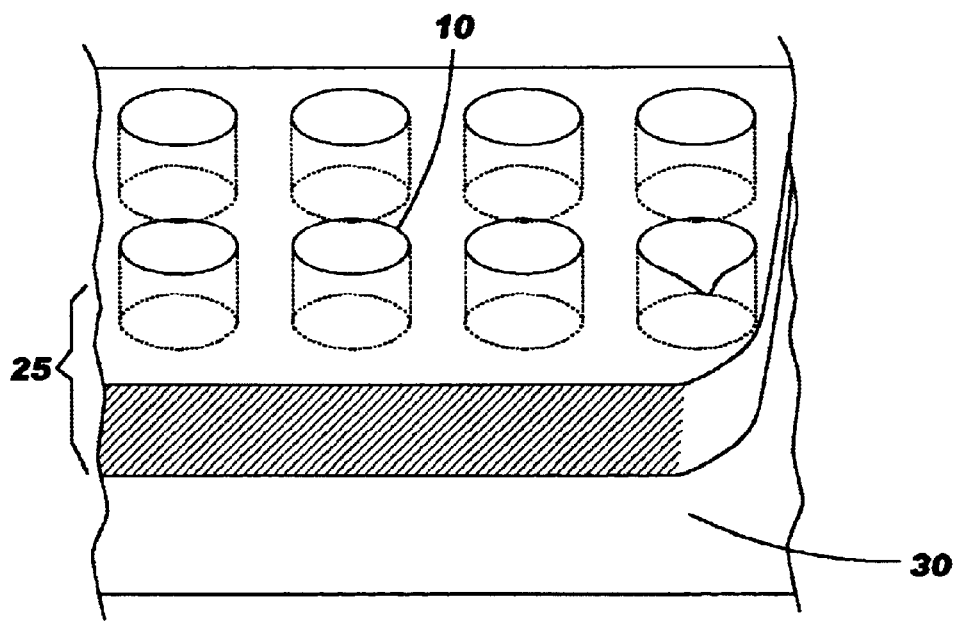
FIG. 5 illustrates a perspective view of the SEM image of FIG. 4.

FIG. 5 is an SEM image showing a perspective (52 deg. tilt) view showing milled region 30 with resist removed, exposing a cross-section 25. It is clear that the entire profile of the contact holes 10 can be seen transparently through the section of resist material of thickness 20. Both FIG. 4 and FIG. 5 are images of the same sample, using 15 kev, but at different angles.

Figure 6:
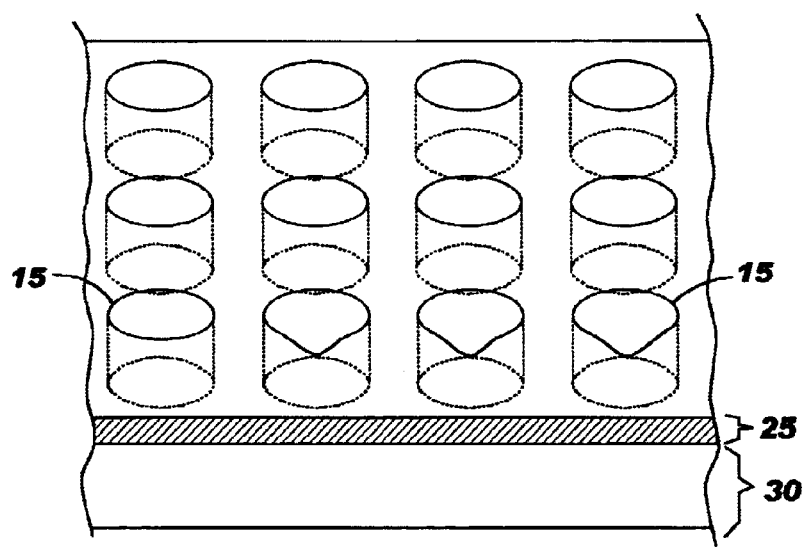
FIG. 6 illustrates a perspective view of a modified contact hole profile in the resist.

FIG. 6 shows an SEM image showing a perspective view (tilt angle 52 deg) of a milled region 30, leaving cross-section 25, through which a transparent image of contact holes 15 can be seen. This figure shows another example of the result of the invention, but in this case the contact holes 15 have a profile with a lip at the top.

Alternatively, by means of a dual beam (DB) tool, a sample of silicon wafer is provided with metal coating if deemed necessary, a specific feature on the wafer is then cross-sectioned with an ion beam, such as a focused ion beam (FIB) which may be a gallium beam, and finally the cross-sectioned feature is examined with an SEM column on the same DB tool.

1. FIB cross-sectioning with selective carbon mill (SCM):

Move the stage 22 to the interested feature inside Field of View (FOV) of 20 um to 40 um. Obtain a relatively fast scan image to confirm the feature is inside the FOV, whereby it is better to be near the center.

Select the beam patterning mode of Cleaning Cross-Section. A Gallium ion beam current of 10 PA is used for the milling. Beam parameter setting is:

Dwell time=0.2, us

Overlap of the spot size=0%

Assumed spot size=100 Å

The milling depth or milling time is so selected that the final milling depth adjacent to the feature is barely deeper then the bottom of the feature of interest, which can minimize the beam damage on the top edge. The milling box size has a width of 3 um and a height of 1 um. The height can be adjusted according the feature depth to make certain that nothing is blocking the SEM during the tilt viewing.

Position the milling box about 300 nm or less offset horizontally from the contact or features of interest. If the target feature to be imaged, such as an interior portion of a contact hole, is interior to a resist feature, such as a contact hole, the milling box may cut through the resist feature (i.e., the contact hole) and positioned offset from the target feature (i.e., the interior portion of the contact hole). The final scan edge of the milling box is the edge closest to the target feature. Depending upon the extent of beam drifting, the milling box placement can vary from sample to sample.

Select SEM as the primary beam with a beam energy in the range of 3 kev to 20 kev. A transparent SEM image magnification as high as 200,000 and tilt angle which is essentially non-vertical, but which is preferably within the range of about 50–60°, can be assumed without charging problem, which can be used for fundamental evaluation and metrology measurement.

From the foregoing, it becomes readily apparent to one skilled in the art that the present invention as described herein is clearly directed to novel and advantageous features not at all disclosed nor suggested in the prior art in that there is a considerable savings of silicon wafers during the non-destructive testing and sampling of the various features, while concurrently avoiding the off-line processing time necessitated in the sampling thereof. Moreover, the invention is applicable to closed, shaped features on resist.

While the invention has been particularly shown and described with respect to preferred embodiments thereof, it will be understood by those skilled in the art that the foregoing and other changes in form and details may be made therein without departing from the spirit and scope of the invention.

What is claimed is:

1. A method of obtaining a transparent image through the intermediary of a scanning electron microscope (SEM), the method comprising:

providing a substrate having a first surface;

forming a resist layer on said first substrate layer; said resist having at least one target feature therein;

forming a milled section in said resist layer, said milled section having an exposed sidewall adjacent to and offset from said at least one target feature at a distance along a surface of said resist layer; and imaging said at least one target feature with a beam projected by said scanning electron microscope (SEM), said SEM beam impinging against the surface of said resist layer at a non-vertical angle in a direction towards said exposed sidewall.

2. A method as claimed in claim 1, wherein said milled section in said resist layer is produced through a focused ion beam (FIB).

3. A method as claimed in claim 1, wherein said SEM beam comprises a primary beam having a beam energy within the range of about 3 kev to 20 kev.

4. A method as claimed in claim 1, wherein said SEM has a beam energy of about 15 kev.

5. A method as claimed in claim 3, wherein said primary beam provides a magnification of up to about 200,000.

6. A method as claimed in claim 1, wherein said SEM beam subtends an angle within the range of about 50–60° relative to the horizontal surface of said resist layer.

7. A method as claimed in claim 2, wherein said SEM scanning is effected in a dual-beam (DB) chamber operating at a subatmospheric pressure of about $8 \times 10^{-7}$ to $6 \times 10^{-3}$ mbar.

8. An arrangement for obtaining a transparent image through the intermediary of a scanning electron microscope (SEM), the arrangement comprising:

a substrate having a first surface;

a resist layer being located on said first substrate layer; said resist having at least one target feature formed therein;

a milled section being provided in said resist layer, said milled section having an exposed sidewall adjacent to and offset from said at least one target feature at a distance along a surface of said resist layer; and at least one target feature being imaged with a beam projected by said scanning electron microscope (SEM), said SEM beam impinging against the surface of said resist layer at a non-vertical angle in a direction towards said exposed sidewall.

9. An arrangement as claimed in claim 8, wherein said milled section in said resist layer is produced by a focused ion beam (FIB).

10. An arrangement as claimed in claim 8, wherein said SEM comprises a primary beam having a beam energy in the range of about 3 kev to 20 kev.

11. An arrangement as claimed in claim 10, wherein said SEM has a beam energy of about 15 kev.

12. An arrangement as claimed in claim 10, wherein said primary beam provides a magnification of up to about 200,000.

13. An arrangement as claimed in claim 8, wherein said SEM beam subtends an angle within the range of about 50–60° relative to the horizontal surface of said resist layer.

14. An arrangement as claimed in claim 8, wherein SEM scanning is effected in a dual-beam (DB) chamber operating at a subatmospheric pressure of about $8 \times 10^{-7}$ to $6 \times 10^{-3}$ mbar.

* * * * *